(12) United States Patent
Rajamannan

(10) Patent No.: US 6,372,238 B1
(45) Date of Patent: Apr. 16, 2002

(54) METHOD OF USING IMPLANTS TO FERTILIZE, CONTROL GROWTH AND FUNGAL AND INSECT ATTACK ON BANANA OR PLANTAIN

(76) Inventor: Ambrose H. J. Rajamannan, 2120 Argonne Dr., Minneapolis, MN (US) 55421

( * ) Notice: Subject to any disclaimer, the term of this patent is extended or adjusted under 35 U.S.C. 154(b) by 0 days.

(21) Appl. No.: 09/527,610

(22) Filed: Mar. 17, 2000

(51) Int. Cl.⁷ .......................... A01N 25/00; A01N 59/00; A01N 59/26; A01N 43/64

(52) U.S. Cl. ...................... 424/405; 424/600; 424/601; 424/602; 424/722; 514/383; 504/119; 504/122; 504/124

(58) Field of Search ................................. 424/600, 601, 424/602, 722, 405; 504/119, 122, 124; 514/383

Primary Examiner—Alton Pryor
(74) Attorney, Agent, or Firm—Herman H Bains

(57) ABSTRACT

A process for providing nutrient material for banana and plantain plants, comprising providing a slow release implant containing a banana and plantain nutrient material and implanting the implant into banana or plantain plants whereby the nutrient is slowly released into the plant over a period of time.

14 Claims, No Drawings

METHOD OF USING IMPLANTS TO FERTILIZE, CONTROL GROWTH AND FUNGAL AND INSECT ATTACK ON BANANA OR PLANTAIN

FIELD OF THE INVENTION

This invention relates to the method of providing nutrients to and controlling fungal infections of banana and plantain plants by implanting a slow release implant containing nutrients and fungicides into the banana and plantain plants.

BACKGROUND OF THE INVENTION

Plantain and banana plants are pseudo stems and really are the leaves of the plant and consist of mostly cells with high content of water matter which take the nutrients from the roots and the rhizome under ground to the leaves for photosynthesis and growth and then translocates these carbohydrates and nutrients to the fruit. When the fruit is mature the nutrients left over are then translocated to the young (sucker) offspring again via the rhizome.

Nutrients for the growth and production of fruits are conventionally obtained from the soil, whether applied as fertilizers manually or from soil inherent fertility.

When fertilizers are applied to the ground up to 80% of these applied nutrients can be locked up in the soil and made insoluble or unavailable. The cost to the producer because of this drastic reduction of available nutrients of these applied fertilizers is high and has been accepted as inevitable cost of producing the fruits.

Recently liquid forms of nutrients have been injected into the pseudo stem of the banana or Plantain plant to supplement the soil-applied nutrients. There is a problem with this method.

Since the banana plantain is grown in high rainfall tropical areas around the world, the pseudo stem has a high aquatic pressure within the extra cell structure, that wherever liquid fertilizers are injected into the pseudo stem, significant portion of this injected material is expelled out of the pseudo stem through the injected opening. There is a need to find a method to introduce nutrients into this high aquatic system on a continuous basis inside the pseudo stem without having it excreted out and therefore having to inject these nutrients into the pseudo stem very frequently at high labor costs.

Conventionally, fungicides to control fungal disease prevalent in bananas and plantains have to be sprayed by airplanes, frequently, from once every month to once every week.

Of this applied pesticides, a significant portion is lost to drift, falling on the ground or washing off by the high rainfall in the tropical countries where bananas are grown. Therefore only a small percentage of the sprayed fungicide actually goes into the banana or plantain plant.

Besides the environmental impact of these aerially applied pesticides, workers in the banana plantation are also exposed to these aerially applied chemicals.

SUMMARY OF THE INVENTION

An object of this invention is to provide a novel method of providing nutrients and for controlling pathogens infecting banana and plantain plants by implanting a slow release implant containing nutrients and/or pesticides and fungicides into banana and plantain plants. Nutrients and/or pathogen controlling substances are slowly released into the banana or plantain plants over a period of time thereby obviating the need to fertilize and/or apply a pathogen controlling substance to the banana and plantain plants being treated.

DESCRIPTION OF THE PREFERRED EMBODIMENT

The novel method involves the introduction into these pseudo stem or the rhizome of the banana or plantain plant an implant with nutrients that can be solubilized slowly by the aqueous material of these plants and taken up to the leaves and or down the rhizome and supplement the nutrients that is being taken up by the roots of these plants.

These implants can be of various designs that will be elaborated below.

These implants can have plant growth regulators or nutrients or pesticide to systemically increase the resisting ability of these plants against fungal or insect infections.

The implants can be bare sticks that are composed of pesticides and or various macro and micronutrients and or plant growth regulators and or vitamins bound together by a polymer or some other adhesive material.

Implants can be plastic or similar material either porous or semi permeable packed with dry or gel nutrients or pesticides or growth regulators.

Implants can be soluble get capsules with liquid nutrients and or pesticides or plant growth regulators.

Implants can be, also a flexible fiber with nutrients and or pesticides attached to the fiber that can be introduced into the pseudo stem.

Implants can be pellets that can be implanted or shot into pseudo stem by a propellant mechanism.

The opening entry to the pseudo stem can also be closed to the outside, after insertion of an implant with a sealant, stopper or bandage.

Implants clan be nutrients and or pesticides in a slow release gel that can be placed inside the pseudo stem by an injectable needle with a piston.

The nutrient material for the banana and plantain plants may include conventional nutrient products, 20-20-20 formulation (nitrogen, phosphorus and potassium) or, nitrogen, phosphorus or potassium may be used alone. Various combinations of nitrogen, phosphorus,,potassium, calcium, magnesium, zinc, manganese, iron, molybdenum, copper, sulfur and boron may be used in the nutrient implant.

The implant may also include a growth regulator including the commercial growth regulators Cytokinin, Gibberellins, and Auxins. The growth regulators may be used alone or in combination with the nutrients.

The implants may also include systemic pesticides for controlling fungi, insects or nematodes. Commercial systemic pesticides which are preferably used include Calixin, Baycor, Seco, Indar and Bankit.

EXAMPLE 1

Nutrients applied by ground around the dozen banana mats at 10 grams per plant and dry implant nutrient sticks were inserted into the pseudo stem of a dozen banana plants that were three months old. These plants were new plantings (i.e. first generation). The amount of nutrients applied by implants was 1 gram per plant with a 20-20-20 formulation. The nutrients applied on the ground were 10 gram of a 20-20-20 formulation (20% nitrogen, 20% phosphate, 20% potassium).

Leaf analysis was taken before all 2-dozen plants before applying the nutrients and 2 weeks after applying the nutrients.

The average results of the tissue analysis are shown in Table 1.

TABLE 1

|  | Before | | | 2 Weeks after | | |
| --- | --- | --- | --- | --- | --- | --- |
|  | N | P | K | N | P | K |
| Soil Applied | 2.6 | 0.76 | 3.6 | 2.7 | 0.8 | 3.8 |
| Implant | 2.7 | 0.65 | 3.0 | 3.0 | 1.0 | 4.0 |

The implant clearly increased the nitrogen, phosphorous and potassium within 2 weeks.

EXAMPLE 2

Six (6) months old banana plants were sprayed with Baycor, Calixin, Seco, Indar, Bankit, which are well known systems (i.e. they work through the plant by systemically invigorating the plant or by maintaining sufficient concentrations of the pesticide to prevent or kill the fungus that invades the cell of the plant.

In a series of experiments, 6 banana plants were used as controls and 6 banana plants were used as treated. Each set of the dozen plants was used for five well known fungicides.

Control plants were sprayed with recommended amounts of the specific fungicide every 10 days.

The treated plants were implanted with the same fungicide impregnated in an acrylic polymer implant. The content of the implant was $1/10^{th}$ of the amount used by foliar application.

The trial was continued for 3 months and infection by sigatoka was measured. The average results are shown in Table 2.

TABLE 2

|  | Conventional Foliar | | | | | |
| --- | --- | --- | --- | --- | --- | --- |
|  | After 1st Month | 2nd Month | 3rd Month | Implants | | |
| Calixin | 15% | 17% | 20% | 5% | 7% | 8% |
| Baycor | 10% | 12% | 15% | 3% | 6% | 8% |
| Seco | 9% | 13% | 16% | 3% | 7% | 9% |
| Indar | 12% | 13% | 15% | 4% | 7% | 9% |
| Bankit | 10% | 15% | 20% | 2% | 5% | 7% |

The implanted banana plants showed the lowest infection ever into the 3rd month after plant.

What is claimed is:

1. A process for providing nutrient material for banana and plantain plants, comprising
   providing a slow release implant containing a banana and plantain nutrient material selected from the group consisting of nitrogen, phosphorus, potassium, calcium, magnesium, zinc, manganese, iron, molybdenum, copper, sulfur, and boron,
   and implanting the implant into banana or plantain plants whereby the nutrient is slowly released into the plant over a period of time.

2. The process as defined in claim 1 wherein the implant also contains a substance for systemically controlling banana and plantain plant pathogens are selected from fungi, insects and nematodes whereby the pathogen controlling substance is slowly released into the plant over a period of time.

3. The process as defined in claim 1 wherein the implant also contains a plant growth regulator.

4. The process as defined in claim 2 wherein the pathogen controlling substance is selected from the group consisting of Calixin, Baycor, Seco, Indar, and Bankit.

5. The process as defined in claim 3 wherein the growth regulator is selected from the group consisting of Cytokinin, Gibberellins and Auxins.

6. The process as defined in claim 1 wherein the implant is formed of a material selected from the group consisting of powder, gel or fiber.

7. The process as defined in claim 6 wherein said implant comprises a semi-permeable capsule.

8. The process as defined in claim 6 wherein said implant comprises a pellet.

9. The process as defined in claim 6 wherein said implant comprises a polymer bound fibrous stick.

10. A process for controlling pathogens which attack banana and plantain plants, comprising providing a slow release implant containing a substance for systemically controlling banana and plantain plant pathogens are selected from fungi, insects and nematodes, said pathogen controlling substance being selected from the group consisting of Calixin, Baycor, Seco, Indar and Bankit, the pathogen controlling substance being slowly released into the banana or plantain plant over a period of time.

11. A process for providing plant growth regulators for banana and plantain plants, comprising
    providing a slow release implant containing a plant growth regulator for banana and plantain plants selected from the group consisting of Cytokinin, Gibberellins, and Auxins, the growth regulator being slowly released into the banana or plantain over a period of time.

12. A process for providing nutrient, pathogen controlling substance, and plant growth regulator to banana and plantain plants, comprising
    providing a slow release implant containing a banana and plantain nutrient material selected from the group consisting of nitrogen, phosphate, potassium, calcium, magnesium, zinc, manganese, iron, molybdenum, copper, sulfur and boron,
    said implant containing a systemic pathogen controlling substance for pathogens are selected from fungi, insects and nematodes which attack banana and plantain
    the pathogen containing substance selected from the group consisting of calixin, Baycor, Seco, Indar, and Bankit,
    the implant containing a plant growth regulator selected from the group consisting of Cytokinin, Gebberellins, and Auxins whereby the nutrient material, pathogen controlling substance and growth regulator will be slowly released into the banana or plantain plant over a period of time.

13. A process for providing nutrient material for banana and plantain plants, comprising
    providing a slow release implant containing a banana and plantain nutrient material comprising 20% nitrogen, 20% phosphate and 20% potassium.
    and implanting the implant into banana and plantain plants whereby the nutrient is slowly released into the plant over a period of time.

14. A process for providing nutrient, pathogen controlling substance, and a plant growth regulator to banana and plantain plants, comprising
    providing a slow release implant containing a banana and plantain nutrient material comprising 20% nitrogen, 20% phosphate, and 20% potassium,
    said implant containing a systemic pathogen controlling substance for pathogens are selected from fungi, insect and nematodes which attack banana and plantain, the pathogen containing substance selected from the group consisting of Calixin, Baycor, Seco, Indar, and Bankit, the implant containing a plant growth regulator selected from the group consisting of Cytokinin, Gebberellins, and Auxins whereby the nutrient material, pathogen controlling substance and growth regulator will be slowly released into the banana or plantain plant over a period of time.

* * * * *